US005478579A

United States Patent [19]

Sawruk

[11] Patent Number: 5,478,579
[45] Date of Patent: Dec. 26, 1995

[54] METHOD FOR TREATMENT OF OSTEOPOROSIS

[75] Inventor: Stephen Sawruk, Lanoka Harbor, N.J.

[73] Assignee: Biodyn Medical Research, Inc., Nutley, N.J.

[21] Appl. No.: 95,738

[22] Filed: Jul. 21, 1993

Related U.S. Application Data

[63] Continuation-in-part of Ser. No. 897,003, Jun. 1, 1992, abandoned, which is a continuation-in-part of Ser. No. 651,189, Feb. 6, 1991, abandoned.

[51] Int. Cl.⁶ .......................... A01N 43/04; A61K 31/715; C07H 15/00; C07G 3/00
[52] U.S. Cl. ...................... 424/535; 514/25; 514/54; 536/8; 536/4.1; 536/1.11
[58] Field of Search ............................ 424/535, 468, 424/195.1, 180, 535; 514/734, 25, 28, 728, 54; 536/8, 4.1, 1.11

[56] References Cited

U.S. PATENT DOCUMENTS

| | | | |
|---|---|---|---|
| 2,681,907 | 6/1954 | Wender et al. | 536/8 |
| 3,420,815 | 1/1969 | Courbat | 536/8 |
| 3,888,842 | 6/1975 | Cazaux et al. | 536/8 |
| 4,255,563 | 3/1981 | Wakihira et al. | 536/8 |
| 4,410,515 | 10/1983 | Holick et al. | 424/180 |
| 4,617,293 | 10/1986 | Wahlig et al. | 536/8 |
| 4,753,929 | 6/1988 | Matsumoto et al. | 536/8 |
| 4,774,229 | 9/1988 | Jordan | 514/25 |

OTHER PUBLICATIONS

Sankara et al; Melcitrin–A New Myricetin Glycoside from the Flowers of Melia azadirachta; Indian J. Chem., vol. 10 (Apr. 1972).
Wolf; Flavonoid Diversity & Endemism in Arnica Subgenus Austromontana; Biochem Systm. Ecol. 12(2); 1984.
Tierri, "The Way of Herbs" Unity Press, Santa Cruz Calif. 1980.

Primary Examiner—Michael G. Wityshyn
Assistant Examiner—Louise N. Leary
Attorney, Agent, or Firm—Klauber & Jackson

[57] ABSTRACT

A method for orally inducing and enhancing the absorption of calcium into mammalian bone tissue comprises the administration of an effective dose of a flavonol aglycone glycoside in combination with nutritional calcium. Various herbal sources are shown. Potassium gluconate may be added to the system as an adjuvant.

19 Claims, No Drawings

METHOD FOR TREATMENT OF OSTEOPOROSIS

REFERENCE TO RELATED APPLICATIONS

The present application is a continuation-in-part of U.S. Ser. No. 07/897,003, filed Jun. 1, 1992, now abandoned, which is a continuation-in-part of U.S. Ser. No. 07/651,189, filed Feb. 6, 1991.

BACKGROUND OF THE INVENTION

This invention relates to methods and compositions for inducing and enhancing the absorption of calcium into mammalian tissue, a phenomenon which is also known as ossification. As such, the present invention relates to a method of treatment of metabolic calcium and other mineral deficiencies in bone tissue. A typical, and most important deficiency, is osteoporosis. Osteoporosis is defined as an absolute decrease in bone tissue mass wherein the remaining bone is morphologically normal.

The present invention utilizes a family of a naturally occurring compounds, namely, flavonol aglycone glycosides, which possesses particular value in facilitating ossification of mammalian bone tissue, i.e., in facilitating the absorption of calcium into mammalian bone tissue, thus reversing the effects of osteoporosis.

The use of the quercetin species of flavonol aglycone glycosides in the treatment of other human medical problems has been recognized. More particularly, U.S. Pat. No. 3,420,815 to Courbat and U.S. Pat. No. 3,888,842 to Cazaux both discuss the value of quercetin and quercetin glycosides in the treatment of circulatory disorders.

The use of flavonoid phosphate salts of aminoglycosides to treat bacterial pathology of the bone is recited in U.S. Pat. No. 4,617,293 to Wahlig et al. Wahlig et al. utilize a fibrin/antibiotic gel prepared by mixing a fibrinogen solution, a thrombin solution and a flavonoid phosphate of an aminoglycoside antibiotic. The thrombin solution optionally includes a calcium salt to enhance its clotting abilities.

Quantitative analysis and, more particularly, thin plate chromatography, has determined that a number of naturally occurring herbs constitute usable sources of flavonol aglycone glycosides. Such herbs are more fully discussed below. However, with respect to the prior art, the literature of herbal medicine and, more particularly, the book entitled *The Way of Herbs* by Tierri, Unity Press, Santa Cruz, Calif. 1980, states that the herb *equisetum arvense* (field horsetail), is a source of quercetin glycoside known as isoquercitrin, that has been employed in primitive cultures to promote more rapid healing of fractured bones. However, the treatment of a trauma-induced condition such as a bone fracture bears little relationship to the treatment of a degenerative disease, such as osteoporosis, that is metabolic in character.

SUMMARY OF THE INVENTION

The present invention relates to a method for orally inducing and enhancing the absorption of calcium into mammalian bone tissue to thereby effect the ossification of such tissue. Such method comprises the step of periodically orally administering to a patient in need of calcium, therapy an effective dose of a flavonol aglycone glycoside in combination with additional calcium.

The administration of the flavonol aglycone glycoside utilized in the invention is typically in the range of between about 50 and 250 mg. per day. Numerous natural sources of species of flavonol aglycone glycoside are available which can be utilized to formulate compositions which include calcium. Potassium gluconate may be optionally added as an adjuvant to the aglycone glycoside and calcium.

It is an object of the present invention to provide an herbal based medicinal composition effective in the treatment of calcium deficiencies in mammalian bone.

Another object is to provide a cost-effective method of strengthening human bone and related tissue, such as nails and teeth, using the herbal based medicinal composition of the present invention.

It is a further object to provide a safe, effective oral dosage regimen for the composition that is self-administered to ensure patient compliance.

The above and yet other objects and advantages of the present invention become apparent and are hereinafter set forth in the Detailed Description of the Invention and Claims appended herewith.

DETAILED DESCRIPTION OF THE INVENTION

The present invention is the result of research with a certain herbs which, upon analysis by thin plate chromatography, were all determined to possess one or another species of a flavonol aglycone glycoside.

Flavonol aglycone glycosides comprise a compound having two benzene rings connected by a chain of three carbon atoms and an oxygen bridge. More particularly, the molecular structure of a flavonol aglycone glycoside is shown in Formula I below:

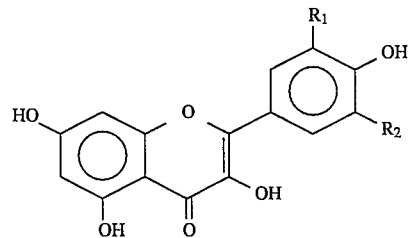

wherein $R_1$ and $R_2$ are independently hydrogen, hydroxy or methoxy group.

Those flavonol aglycone glycosides which appear in nature are the result of different attachments to the second benzene ring in the areas marked $R_1$ and $R_2$ in accordance with the following Table:

| $R_1$ | $R_2$ | Aglycones | Glycosides |
|---|---|---|---|
| OH | H | Quercetin | Q-3-O-galactoside (hyperoside) |
| | | | Q-3-O-glucoside (isoquercitrin) |
| | | | Q-3-O-rhamnoside (quercitin) |
| | | | Q-3-O-rutinoside (rutin) |
| H | H | Kaempferol | K-3-O-glucoside (astragalin) |
| OH | OH | Myricetin | M-3-O-digalactoside |
| $OCH_3$ | H | Isorhamnetin | I-3-O-rutinoside (narcissin) |

From the above structural formula I, it may be appreciated that flavonol aglycone glycosides possess four species, namely, quercetin, kaempferol, myricetin, and isorhamnetin. Quercetin, in turn, possesses four subspecies, these known as hyperoside, isoquercitrin, quercitin, and rutin.

Experiments undertaken by the inventor have involved the use of herbs containing, as their primary active ingredient, said isoquercitrin, which is from the quercetin glycoside species of flavonol aglycone glycoside.

Herbs known to contain significant quantities of quercetin glycoside include *arnica montana* (commonly known as mountain tobacco), *crataegifolium* (commonly known as Hawthorne flowers), *farfarae flos* (commonly known as colts foot flowers), *primulae flos* (commonly known as primrose), *pruni spinosae flos* (commonly known as black thorn flowers), *sanbuci flos* (commonly known as elderflowers), *tiliae flos* (commonly known as lime flowers), *petulae flioum* (commonly known as birchleaves), *anserinae* (commonly known as silverweed), *equisetum arvense* (commonly known as horsetail), *vigaureae* (commonly known as goldenrod), and *violae tricoloris* (commonly known as wild pansy).

In most of the above recited herbs, the quercetin glycoside will appear in combination with certain other components which, it is believed, are of certain value in the present calcium absorption therapy. Those additional herbal components believed to be of value are galuteolin and betasitosteral.

Thus, the present invention utilizes a flavonol aglycone glycoside, for instance, a quercetin glycoside, administered orally with a 500–1500 mg per day dose of nutritional calcium. Typical dosages of the flavonol aglycone glycosides are about 50 and 250 mg. per day.

Also, it has been found that the effectiveness of the method is further enhanced if an adjuvant, such as potassium gluconate, is added. Thus, a highly preferred method involves the further administration of potassium gluconate at a dosage of 50 to 250 mg. per day.

While not wishing to be bound to any particular theory, it is believed that the flavonol aglycone glycosides such as quercetin glycosides are believed to afford an advantageous function through a chelation delivery system. A chelate is defined as a benzene ring, usually containing a metal ion, held to the ring by coordination bonds. Coordination bonds are quasi-chemical, however, weaker than either a valence or an ionic bond. Such coordination bonds enable chelates to hold metal ions (chemically speaking, calcium is a metal) and to effectively deposit the ions into certain tissues.

In terms of molecular structure, a flavonol possesses a benzene ring structure having available bonds to function as a chelate. That is, flavonols, by their particular molecular structure, are capable of holding and delivering certain minerals, including calcium, to mammalian bond tissue. Also, bone tissue would, in any event, naturally absorb flavonol glycosides from the bloodstream. This is particularly understandable in that a glycoside, by definition, comprises a sugar derivative containing a non-sugar group attached through an oxygen or nitrogen bond. In the case of an aglycone glycoside, the bond is one of oxygen. In that virtually that every cell in the human body makes use of sugar, it is apparent that a flavonol aglycone glycoside would constitute an effective delivery system for any needed metallic mineral.

The present invention also includes compositions for orally inducing and enhancing the absorption of calcium into mammalian bone in a patient in need of such treatment which consist essentially of:

(a) flavonol aglycone glycoside in an amount effective to induce and enhance the absorption of calcium into mammalian bone;

(b) an effective dose of nutritional calcium; and (c) pharmaceutically acceptable and pharmacologically inactive excipients.

Preferred compositions comprise the flavonol aglycone glycoside in an amount of 50–250 mg/daily dose and nutritional calcium in an amount of about 500–1500 mg/daily dose. A typical formulation can contain the entire daily dose, but more typically will contain an amount calculated to provide the daily dose when administered 2 or 3 times per day. Such a dosage regimen provides for self-administration by the patient at meals, for instance.

The composition can preferably also contain potassium gluconate in an amount of 50–250 mg/daily dose.

The particular dose for each patient will depend upon the particular flavonol aglycone glycoside employed, as well as the age, weight, particular state of health, and sex of the patient.

The preferred method of administration is orally in the form of tablets, capsules and the like. The oral dosage form can be prepared by conventional procedures for making pharmaceutical tablets and capsules, for example, tableting by compression or molding, encapsulation by spray drying, microencapsulation, and the like. The oral dosage form can employ conventional excipients which are pharmaceutically acceptable and pharmacologically inactive, for example, diluents, binders, lubricants, disintegrators, coloring and flavoring agents in addition to the active compounds defined herein. Examples of such excipients are vegetal silica binder, corn starch, gelatin, gums such as carboxymethyl cellulose, acacia and locust bean gum, sugars such as sucrose, dextrose and lactose, salts such as sodium chloride, and the like materials.

The compounds of this invention may be used in the form of liquid compositions suitable for enteral administration, which contain the flavonol aglycone glycosides of the present invention in admixture with an organic or inorganic liquid carrier. For making up such preparations there may be employed substances which do not react with the compounds, such as water, gelatine, lactose, starches, stearic acid, magnesium stearate, stearyl alcohol, talc, tragacanth, acacia, vegetable oils, benzyl alcohols, gums, propylene glycol, polyalkylene glycols or any other known carrier used in the manufacture of such preparations. The latter may be in liquid form, for example, as solutions, suspensions, emulsions and the like. If desired, they may contain auxiliary substances, such as preserving, stabilizing, wetting, emulsifying agents and the like, salts for varying the osmotic pressure, buffers, etc.

EXAMPLE I

A 61 year old female, weight 154 lbs , height 65", considered a high-fracture risk, was provided with a system consisting of two tablets and containing 125 mg of naturally occurring equisetum arvenise including isoquercitrin, that also contained galotelin, betasitosteral and vegetal silica. Each table also contained 125 mg. potassium gluconate and 400 mg. of nutritional calcium.

To study the effect on the subject over a 33-day period of the above regimen, tests of bone density, using a dual photol gadolinium source, were employed. Such studies focused upon the lumbar region of the back of the subject. At the beginning of the 33-day regimen, the subject's bone mineral density possessed a value of 0.765 grams per square centimeter. At the end of the 33-day regimen, the bone mineral density improved to 0.809 grams per square centimeter. This value represented about 73% of what would be a normal value for women of like age.

In the opinion of a diagnostic radiologist, the improvement from 0.765 to 0.809 grams was medically significant. Also, it was the view of the diagnostic radiologist that such an improvement would not have been obtainable through the use of a simple calcium supplement.

These tests were conducted at a facility known as the Montclair Radiological Associates of Montclair, N.J.

EXAMPLE II

Some years prior to the above test, testing with rats was effected by Leberco Testing Inc. of Roselle Park, N.J. These studies covered a period of 75 days. In the course of the rat study, nail density and length were observed and compared with a control group. These studies employed a preparation of the herb equisetum arvenase, nutritional calcium and potassium gluconate. The nutritional calcium was provided in the form of milk. Enhanced nail length and strength, without toxicity, were effected.

This plate chromatography analysis of the equiseteum arvense has indicated the predominant component to be isoquercitrin which, as above noted, is a subspecies of the quercetin glycoside which appears in all of the above noted herbs. As such, it is believed that any of the above set forth sources of quercetin glycoside would comprise a satisfactory source of isoquercitrin.

Accordingly, while there has been shown and described the preferred embodiment of the present invention, it is to be appreciated that the invention may be embodied otherwise than is herein shown and described, and that certain changes may be made, within the scope of the claims appended herewith, without departing from the underlying ides or principles of this invention.

What is claimed is:

1. A method for orally inducing and enhancing calcium absorption into mammalian bone tissue in a patient in need of such treatment comprising the periodic administration of a composition consisting essentially of:

(a) a flavonol aglycone glycoside in an amount effective to induce and enhance the absorption of calcium into mammalian bone tissue;

(b) an effective dose of nutritional calcium; and (c) pharmaceutically acceptable and pharmacologically inactive excipients.

2. The method of claim 1, in which said glycoside is administered in a daily dose of about 50 to about 250 milligrams; and said calcium is administered in a daily dose of about 500 to about 1500 milligrams.

3. The method of claim 2 wherein said flavonol aglycone glycoside is selected from the group consisting of quercetin, kaempferol, myricetin and isorhamnetin.

4. The method of claim 2 wherein said flavonol aglycone glycoside is isoquercitrin.

5. The method of claim 2 in which said flavonol aglycone glycoside comprises an extract of an herb selected from the group consisting of *arnica montana, crataegifolium, farfarae flow, primulae flos, pruni spinosae flos, sanbuci flos, tiliae flow, petulae flioum, anserinae, equisetrum arvense, vigaureae,* and *violae tricoloris.*

6. A method for orally inducing and enhancing calcium absorption into mammalian bone tissue in a patient in need of such treatment comprising the periodic administration of a composition consisting essentially of:

(a) a flavonol aglycone glycoside administered in a daily dose of about 50 to about 250 mg;

(b) nutritional calcium administered in a daily dose of about 500 to about 1500 mg;

(c) pharmaceutically acceptable and pharmacologically inactive excipients; and (d) potassium gluconate administered in a daily dose of about 50 to about 250 mg.

7. The method of claim 6 in which said flavonol aglycone glycoside is selected from the group consisting of quercetin, kaempferol, myricetin and isorhamnetin.

8. The method of claim 7 wherein said flavonol aglycone glycoside is isoquercitrin.

9. The method of claim 6 in which said flavonol aglycone glycoside comprises an extract of an herb selected from the group consisting of *arnica montana, crataegifolium, farfarae flow, primulae flos, pruni spinosae flos, sanbuci flos, tiliae flow, petulae flioum, anserinae, equisetrum arvense, vigaureae,* and *violae tricoloris.*

10. The method of claim 1 wherein the mammalian bone tissue has, or is suspected of having, osteoporosis.

11. A pharmaceutical composition for the treatment of osteoporosis in mammalian bone tissue consisting essentially of:

(a) a flavonol aglycone glycoside in an amount effective to induce and enhance the absorption of calcium into mammalian bone tissue;

(b) an effective dose of nutritional calcium; and (c) pharmaceutically acceptable and pharmacologically inactive excipients.

12. The composition according to claim 11 wherein said flavonol aglycone glycoside is present in amount of 50–250 mg/daily dose and said nutritional calcium is present in an amount of 500–1500 mg/daily dose.

13. The composition of claim 12 in which said flavonol aglycone glycoside comprises an extract of an herb selected from the group consisting of: *arnica montana, crataegifolium, farfarae flow, primulae flos, pruni spinosae flos, sanbuci flos, tiliae flow, petulae flioum, anserinae, equisetrum arvense, vigaureae,* and *violae tricoloris.*

14. The composition according to claim 11 wherein said flavonol aglycone glycoside is selected from the group consisting of quercetin, kaempferol, myricetin and isorhamnetin.

15. The composition of claim 14 wherein said flavonol aglycone glycoside is isoquercitrin.

16. A pharmaceutical composition for the treatment of osteoporosis in mammalian bone tissue consisting essentially of:

(a) a flavonol aglycone glycoside present in the amount of 50–250 mg/daily dose;

(b) nutritional calcium present in the amount of 500–1500 mg/daily dose;

(c) pharmaceutically acceptable and pharmacologically inactive excipients; and (d) potassium gluconate in an amount of about 50 to about 250 mg/daily dose.

17. The composition of claim 16 in which said flavonol aglycone glycoside is selected from the group consisting of quercetin, kaempferol, myricetin and isorhamnetin.

18. The composition of claim 17 in which said flavonol aglycone glycoside is isoquercitrin.

19. The composition of claim 16 in which said flavonol aglycone glycoside comprises an extract of an herb selected from the group consisting of *arnica montana, crataegifolium, farfarae flow, primulae flos, pruni spinosae flos, sanbuci flos, tiliae flow, petulae flioum, anserinae, equisetrum arvense, vigaureae,* and *violae tricoloris.*

* * * * *